(12) United States Patent
Dayeh et al.

(10) Patent No.: US 11,056,517 B2
(45) Date of Patent: Jul. 6, 2021

(54) MONOLITHIC THIN FILM ELEMENTS AND PERFORMANCE ELECTRONICS, SOLAR POWERED SYSTEMS AND FABRICATION

(71) Applicant: The Regents of the University of California, Oakland, CA (US)

(72) Inventors: Shadi A. Dayeh, San Diego, CA (US); Yun Goo Ro, La Jolla, CA (US); Namseok Park, La Jolla, CA (US); Atsunori Tanaka, La Jolla, CA (US); Siarhei Vishniakou, La Jolla, CA (US); Ahmed Youssef, La Jolla, CA (US); James Buckwalter, San Clemente, CA (US); Cooper Levy, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 804 days.

(21) Appl. No.: 15/556,542

(22) PCT Filed: Mar. 10, 2016

(86) PCT No.: PCT/US2016/021814
§ 371 (c)(1),
(2) Date: Mar. 1, 2018

(87) PCT Pub. No.: WO2016/145220
PCT Pub. Date: Sep. 15, 2016

(65) Prior Publication Data
US 2018/0040649 A1 Feb. 8, 2018

Related U.S. Application Data

(60) Provisional application No. 62/130,870, filed on Mar. 10, 2015.

(51) Int. Cl.
| | | |
|---|---|---|
| *B81C 1/00* | (2006.01) | |
| *H01L 31/0352* | (2006.01) | |
| *H01L 31/047* | (2014.01) | |
| *H01L 31/042* | (2014.01) | |
| *H01L 27/142* | (2014.01) | |

(Continued)

(52) U.S. Cl.
CPC .......... *H01L 27/142* (2013.01); *A61B 5/6802* (2013.01); *B81C 1/00238* (2013.01);
(Continued)

(58) Field of Classification Search
None
See application file for complete search history.

(56) References Cited

U.S. PATENT DOCUMENTS

2008/0003492 A1   1/2008 Bates
2010/0221866 A1*  9/2010 Graham .......... H01L 31/035227
                                                    438/73

(Continued)

OTHER PUBLICATIONS

Blaine R. Copenheaver, International Search Report for Application PCT/US2016/021814, dated Jul. 26, 2016.
(Continued)

*Primary Examiner* — Shannon M Gardner
(74) *Attorney, Agent, or Firm* — Greer, Burns & Crain, Ltd.; Steven P. Fallon

(57) ABSTRACT

Methods and devices that monolithically integrate thin film elements/devices, e.g., environmental sensors, batteries and biosensors, with high performance integrated circuits, i.e., integrated circuits formed in a high quality device layer. Preferred embodiments further monolithically integrate a solar cell array. Preferred embodiments provide pin-size and integrated solar powered wearable electronic, ionic, molecular, radiation, etc. sensors and circuits.

17 Claims, 14 Drawing Sheets

(51) Int. Cl.
*A61B 5/00* (2006.01)
*A61B 5/318* (2021.01)
*A61B 5/369* (2021.01)
*A61B 5/389* (2021.01)

(52) U.S. Cl.
CPC ............... H01L 31/035227 (2013.01); H01L 31/035281 (2013.01); H01L 31/042 (2013.01); H01L 31/047 (2014.12); *A61B 5/318* (2021.01); *A61B 5/369* (2021.01); *A61B 5/389* (2021.01); *A61B 2560/0214* (2013.01); *A61B 2562/028* (2013.01); *A61B 2562/125* (2013.01); *A61B 2562/164* (2013.01); *B81B 2201/0214* (2013.01); *B81C 2203/0792* (2013.01)

(56) References Cited

U.S. PATENT DOCUMENTS

| | | |
|---|---|---|
| 2011/0269264 A1 | 11/2011 | Korevaar et al. |
| 2012/0251034 A1 | 10/2012 | Chen et al. |
| 2013/0040447 A1 | 2/2013 | Swaminathan et al. |
| 2013/0041235 A1 | 2/2013 | Rogers et al. |
| 2014/0361356 A1 | 12/2014 | Yu et al. |
| 2018/0295722 A1* | 10/2018 | Renshaw ............ H01L 51/0035 |

OTHER PUBLICATIONS

Canan Dagdeviren et al., "Conformal piezoelectric energy harvesting and storage from motions of the heart, lung, and diaphragm", PNAS, vol. 111, No. 5, pp. 1927-1932, Feb. 4, 2014.

Jonathan A. Fan et al., "Fractal design concepts for stretchable electronics", Nature Communications, Published Feb. 7, 2014.

Dae-Hyeong Kim et al., "Epidermal Electronics", Science Magazine, vol. 333, pp. 838-843, Aug. 12, 2011.

Sun Jin Kim et al., "A wearable thermoelectric generator fabricated on a glass fabric", Royal Society of Chemistry, Energy and Environmental Science, No. 7, pp. 1959-1965, 2014.

Kwi-Il Park et al., "Highly-Efficient, Flexible Piezoelectric PZT Thin Film Nanogenerator on Plastic Substrates", Advanced Materials, No. 26, pp. 2514-2520, 2014.

* cited by examiner

SENSORS ON LOWER SIDE

MONOLITHIC THIN FILM ELEMENTS AND PERFORMANCE ELECTRONICS, SOLAR POWERED SYSTEMS AND FABRICATION

PRIORITY CLAIM AND REFERENCE TO RELATED APPLICATION

The application claims priority under 35 U.S.C. § 119 and all applicable statutes and treaties from prior U.S. Provisional Application Ser. No. 62/130,870, which was filed on Mar. 10, 2015.

FIELD OF THE INVENTION

A field of the invention is device integration. Additional fields of the invention include environmental sensing and biosensing. Example applications of biosensors of the invention include pin-size smart skin mounts, jewelry, watches, clothing, fitness bands, health-monitoring patches, or flexible electronics, light emitters (displays), and light detectors (imagers) on curved surfaces. Another field of the invention is general sensing, such as gas, ion, radiation, and other types of sensing. More generally, the invention provides for monolithic integration of thin film elements/devices with high performance integrated electronics.

BACKGROUND

Existing physiological recording media such as EEG, EKG and EMG are widely used in modern clinical practice. However, conventional EEG, EKG and EMG recoding systems require bulky and immobile equipment. Large (quarter-sized) sensors must be worn directly on the skin and connected through wires to monitors. Consequently, testing can be performed only in dedicated spaces, like clinical laboratories. A new approach is needed in order to give millions of people the ability to monitor, quantify, and optimize their physical and mental performance outside of the clinical lab facilities.

Typical prior sensor devices require wafer/bump bonding of discrete components and suffer from an associated loss of resolution and performance during the bonding process. Other recent efforts concern conformal tattoo-like electronic sensors that can be co-integrated on elastomeric sheets. See, Kim, D.-H., et al., Epidermal Electronics. Science, 2011. 333(6044): p. 838-843. Kim et al. 2011 uses active devices extended in the form of filamentary serpentine nanoribbons and micro- and nanomembranes that are bonded to an elastomer sheet with separately formed sensors, power coils and RF communication circuits. This device is applied like a tattoo, and would collapse upon itself if the elastomer was removed prior to application to the epidermis. One of the design requirements in such wearable electronics was to carefully adjust the effective Young's modulus and bending stiffness of the resulting layered electronics, and this has restrained the compact integration of the electronic components because the single transistor elements had dimensions that were in millimeter scale. Others have tried to optimize the mechanics of such tattoo-like epidermal electronics. See, Fan, J. A., et al., Fractal design concepts for stretchable electronics. Nat Commun, 2014. 5.

Some prior technologies use stencil printing methods on a flexible substrate or use a specially designed rubber stamp to transfer thin circuit component to a flexible material. This provides challenges to compact integration.

Additional research has concerned self-powered sensor systems. Example systems have been powered by kinetic energy [Park, K.-I., et al., Highly-Efficient, Flexible Piezoelectric PZT Thin Film Nanogenerator on Plastic Substrates. Advanced Materials, 2014. 26(16): p. 2514-2520; Dagdeviren, C., et al., Conformal piezoelectric energy harvesting and storage from motions of the heart, lung, and diaphragm. Proceedings of the National Academy of Sciences, 2014. 111(5): p. 1927-1932], and human body heat energy [Kim, S. J., J. H. We, and B. J. Cho, A wearable thermoelectric generator fabricated on a glass fabric. Energy & Environmental Science, 2014. 7(6): p. 1959-1965] using piezoelectric and thermoelectric materials. The former produces transient power that is dependent on applied pressure and requires continuous movement whereas the latter cannot be used for wearable technologies.

SUMMARY OF THE INVENTION

Embodiments of the invention include methods and devices that monolithically integrate thin film elements/devices, e.g., environmental sensors, batteries and biosensors, with high performance integrated circuits, i.e., integrated circuits formed in a high-quality device layer. Preferred embodiments further monolithically integrate a solar cell array. Preferred embodiments provide pin-size and integrated solar powered wearable electronic, ionic, molecular, radiation, etc. sensors and circuits.

A preferred embodiment is a monolithically integrated device, including a thin film element connected through a dielectric layer to Si based CMOS circuit, wherein the device is less than ~50 μm thick, more preferably less than ~20 μm thick and most preferably in the range of ~10.5 to 11 μm thick. The dielectric is preferably polyimide or parylene C. The device can also include a neutral plane layer. The device can be a sensor device where the thin film element is a read-out circuit. The entire device can be pin-head sized, and is preferably no larger than 0.5 to 0.5 cm. Preferred embodiments further monolithically integrate a solar cell. A microwire array solar cell is opposite the sensors and connected to the Si based CMOS read-out circuit to power the CMOS based read out circuit. The microwires are preferably in the range of 8.5-10 μm long and about 2-3 μm in diameter and include a shallow p-n junction. The sensors of thin film can encompass 20-30% or more of the surface of the of the sensor device.

A preferred method for monolithically integrating an integrated circuit in a device layer of a silicon on insulator substrate with a thin film element includes forming electric connector pads to the integrated circuit in the device layer; forming a dielectric layer over the device layer; opening vias in the dielectric layer aligned with the connector pads; depositing metal in the vias; forming a thin film element on the dielectric layer in contact with the metal; attaching a carrier wafer via a polymer to the thin film element; removing a bulk silicon layer of the silicon on insulator substrate; and removing the carrier wafer.

A preferred method for monolithically integrating an integrated circuit in a device layer of a silicon isolated on a backside by an oxide layer with a solar cell and/or a thin film element includes steps of forming an etching mask patterned to create nanowire solar cell elements in an array on the device layer; etching through the etching mask to form the nanowire solar cell elements; removing the etching mask; smoothing the nanowire solar cell elements; creating a dopant mask; doping a shallow junction to form a junction for both the nanowire solar cell elements and the integrated circuit and removing the dopant mask; forming a gate dielectric layer; and fabricating an integrated circuit with interconnection to the nanowire solar cell elements. The smoothing preferably includes formation of a thin oxide layer and then removing the oxide layer via buffered oxide etch. The doping preferably includes proximity doping that includes spinning a layer of dopant onto a carrier, bringing the carrier into proximity of the nanowire solar cell elements and heating to a doping temperature. Thin film elements can be monolithically added per the methods in the previous paragraph.

DESCRIPTION OF PREFERRED EMBODIMENTS

Figure 1A:
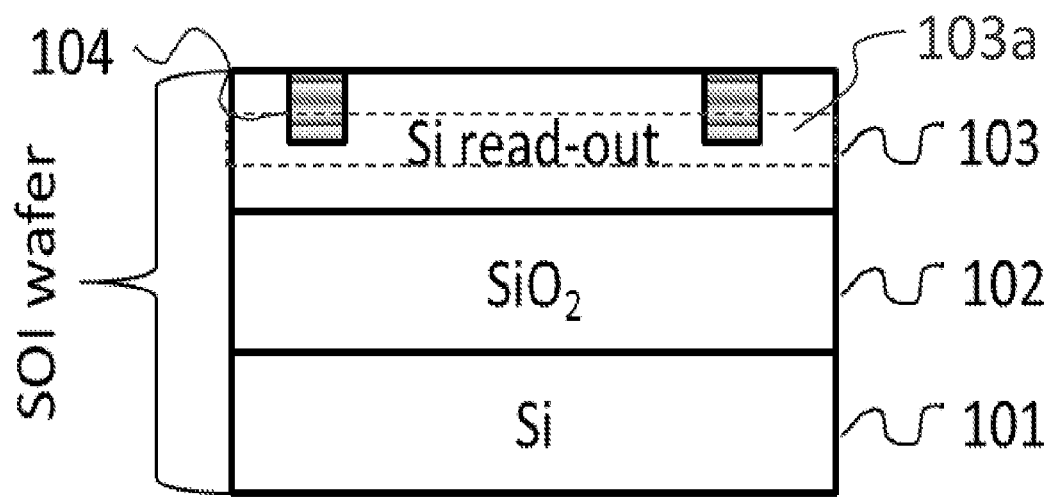
FIG. 1A is a schematic diagram of a CMOS fabrication process in a first preferred embodiment integrated device fabrication method.

The prior approaches discussed in the background for forming thin film biosensors are focused upon sensing over relatively large areas and provide electronics that can stretch with movements of the epidermis. The surface area of the sensors is large enough, usually with feature dimensions above 1 mm or 10s of mm, that normal movements of the epidermis to which the sensor is affixed can apply forces to the sensors that require the sensors to flex, stretch and bend to accommodate such movements of the epidermis. The focus of the prior research known to the inventors has been on flexible sensors and read out circuitry. However, the present inventors have determined and experimentally demonstrated that epidermal electronics need not be integrated over a large enough area to require the electronics to stretch with the epidermis. Instead, highly compact epidermal electronics (with nanometer scale electronics and micrometer-to-millimeter scale sensors and energy harvesting and storage units similar in size to modern computer chips) can occupy very small surface area and move with the skin (rather than stretch with it). Sensor devices provided by preferred embodiments are small enough that the devices are difficult to see without a magnifying lens, and do not alter the appearance of the wearer or compromise comfort of a wearer. Preferred embodiments provide heterogeneous integration in a monolithic fashion on Si and can provide a sensor/monitoring systems. Preferred devices of the invention also provide an integrated power source. State of the art devices like Kim et al. (Science 2011) rely upon a wireless power coil that occupies a substantial footprint and therefore must stretch.

Embodiments of the invention provide a seamless, compact and non-intrusive, high-sampling-speed biomedical sensor for health monitoring. A preferred integration method provides multi-modal, ultra-thin and highly integrated electronic devices that can record from the human skin, process, and transmit electrophysiological data for medical purposes.

Preferred embodiment methods and devices monolithically integrate nanometer scale electronics, such as 0.18 μm CMOS electronics, in high quality epitaxial device layers, with thin film elements, such as sensors, on a common substrate. In additional embodiments, both thin film elements and a power source in the form of a solar cell are monolithically integrated onto a common substrate. Prior sensor devices discussed in the background bond fabricated sensors with larger scale transistors. In preferred embodiments, the scale of the monolithically integrated electronics allows very high performance and high-speed electronics that can process sensed information at a speed that allows the information to be transferred wirelessly. Fabrication methods of the invention are also amendable to large-scale fabrication processes. The methods provide self-aligned features and are fully compatible with processes used in the semiconductor fabrication industry.

Preferred embodiments include a monolithic device fabrication process on a silicon-on-insulator (SOI) substrate with accompanying sensors atop (e.g. Electroencephalography (EEG), Electromyography (EMG), temperature, ionic, pressure, fluid and blood flow, etc), that provide dense multi-modal sensitivity in a very small area while maintaining human comfort. Sensors of the invention can provide for health monitoring without affecting lifestyle or the natural habits of people, especially patients and athletes. Preferred sensors can form systems and can be integrated with commonly worn accessories such as earrings, necklaces, rings, watches, etc, without altering appearance/physiology of the person. Preferred sensors of the invention form systems with amplifying and processing electronics.

Preferred fabrication processes are fully compatible with CMOS processing techniques and provide sub-micron resolution in a highly integrated manner No wet etches are required in preferred methods. Needed etches are accomplished with dry plasma activated etching. Wafer alignment and bonding, which limit resolution to tens of microns, are avoided by preferred embodiments.

In addition to biosensors, embodiments of the invention can integrate thin film batteries, and environmental sensors, such as gas, ion, radiation, and other types of sensors for larger scale applications. Preferred embodiment systems also provide interactive displays formed of transparent layers, pressure sensors and read-out electronics, all on a flexible substrate.

Sensors and systems of the invention have a wide variety of uses and will provide benefit to different groups of people. Example groups of people include clinical patients, athletes, and people interested in self-monitoring. Flexible displays of the invention can include wearable smart skin and be used with smart phones, tablet computers and any form of interactive electronics.

Preferred embodiments combine electrophysiological sensors with readout circuitry on ultra-thin flexible or rigid substrates that are pin-head sized.

Additional preferred embodiments of the invention provide solar-powered high performance electronics in flexible formats. The preferred embodiments integrate power, sensor, and Si circuitry built on silicon chips onto flexible materials. A preferred embodiment includes tall radial junction Si microwire solar cells, electrophysiological sensors, and Si metal-oxide semiconductor field effect transistors (MOSFETs) are integrated side-by-side, and are completely self-powered.

A particular preferred monolithic device fabrication process is conducted on a silicon-on-insulator (SOI) substrate and provides high profile, e.g., 9.5 μm tall, radial junction Si microwire solar cells, electrophysiological sensors, and Si metal-oxide semiconductor field effect transistors (MOSFETs) integrated side-by-side. The solar power conversion efficient Si microwire solar cells are designed to produce enough renewable energy to power circuit elements of Si requiring zero external energy input. The preferred solar-powered system on an SOI platform is embedded on flexible materials which provide flexibility on the system so that it conforms to the uneven surfaces or contours of human body and objects.

Preferred monolithic solar devices of the invention can harvest energy from sunlight to power Si MOSFET circuits with a continuous power density of 14.97 $mW/cm^2$ at 15% power conversion efficiency.

A preferred heterogeneous fabrication and integration process of the invention provides multi-functional and multi-layered devices that are monolithically integrated onto a single handle substrate, and upon completion of the integrated system, the handle substrate is removed. The process can incorporate and integrate multiple circuit components without bump bonding of discrete components.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

Figure 1B:
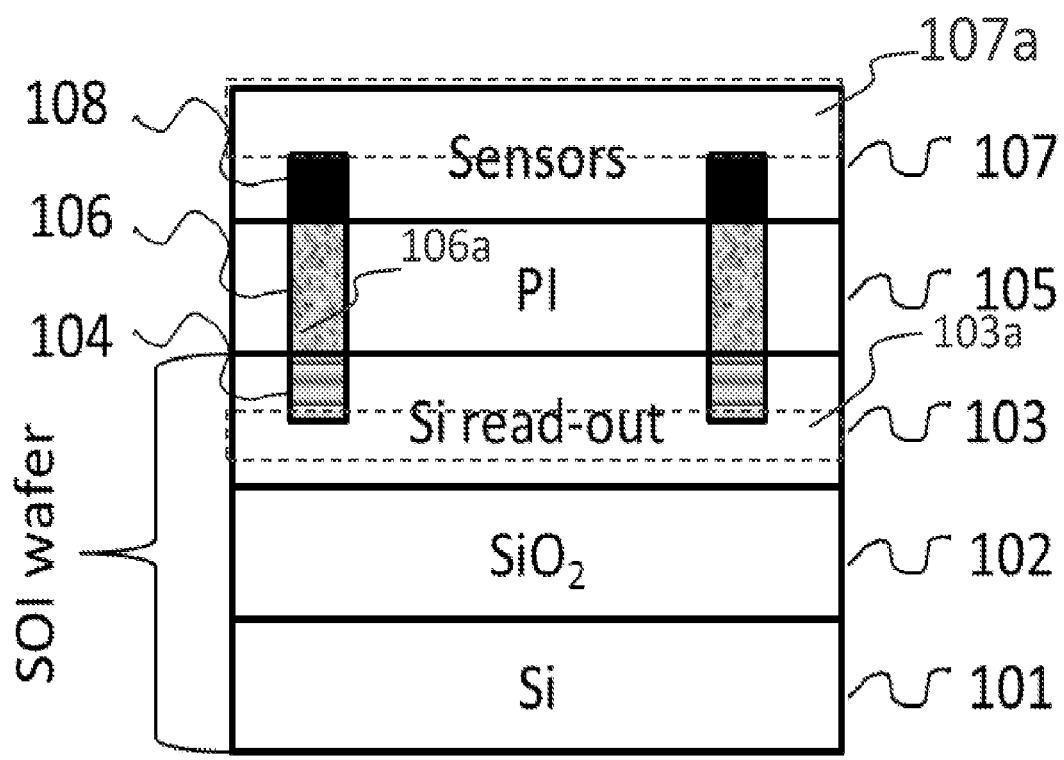
FIG. 1B is a schematic diagram of a through via thin film element, such as a sensor to CMOS circuit electrical connection process of the first preferred embodiment integrated device fabrication method.
Figure 1C:
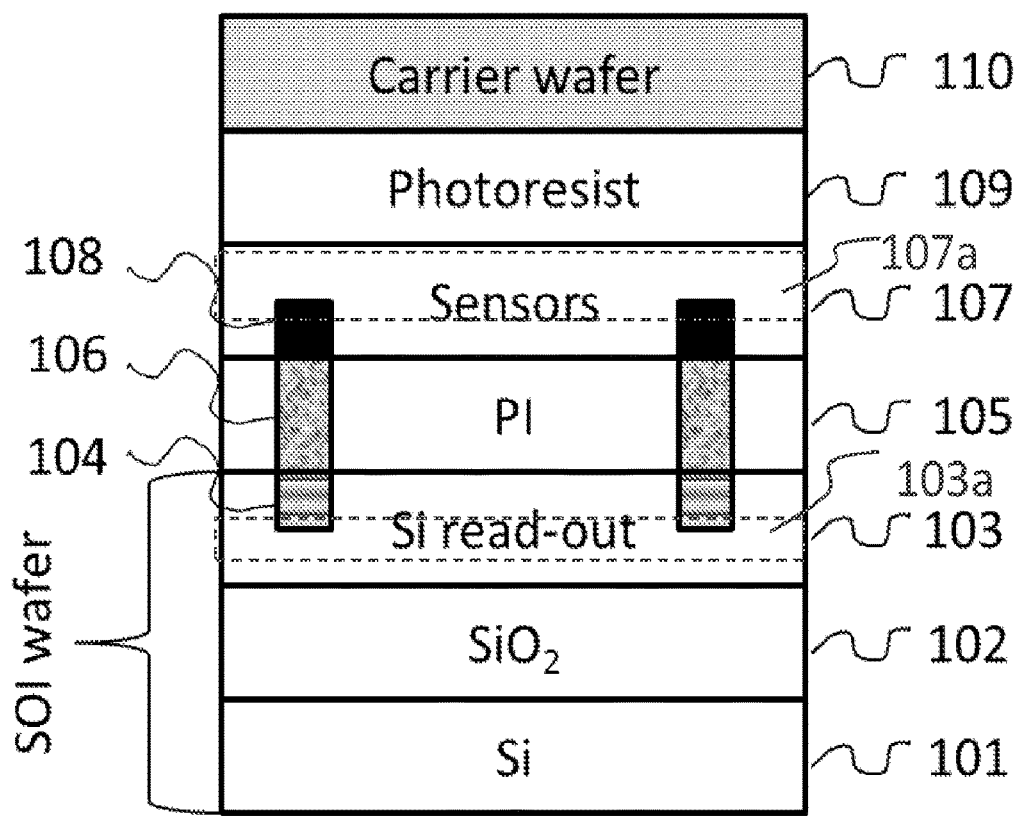
FIG. 1C is a schematic diagram of a carrier wafer bonding process of the first preferred embodiment integrated device fabrication method.
Figure 1D:
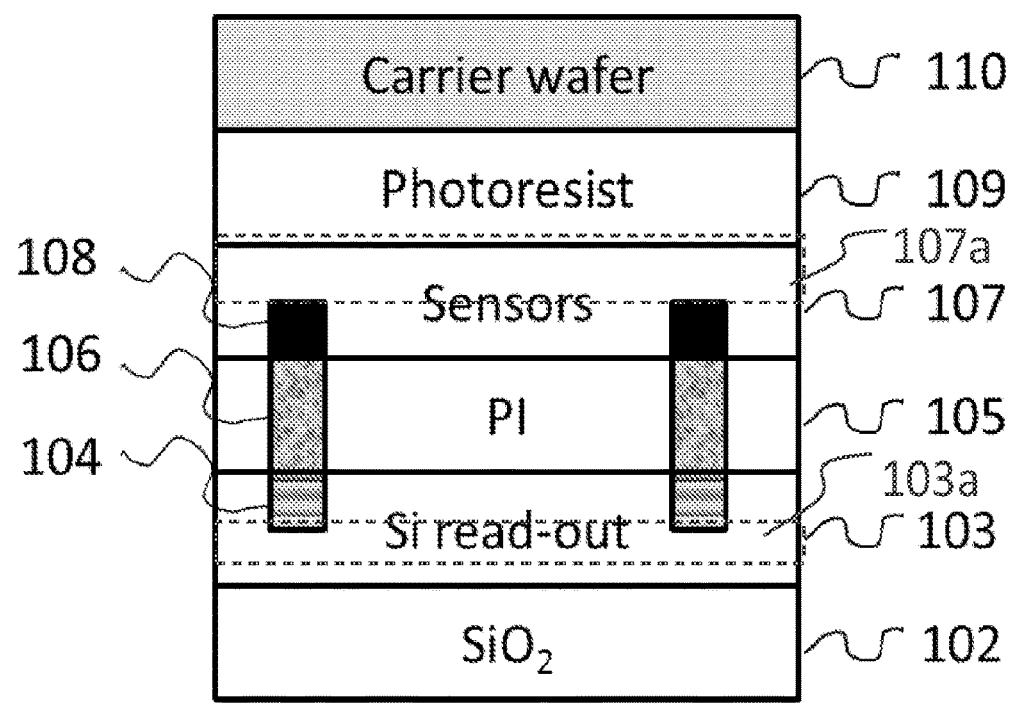
FIG. 1D is a schematic diagram of a layer removal process of the first preferred embodiment integrated device fabrication method.
Figure 1E:
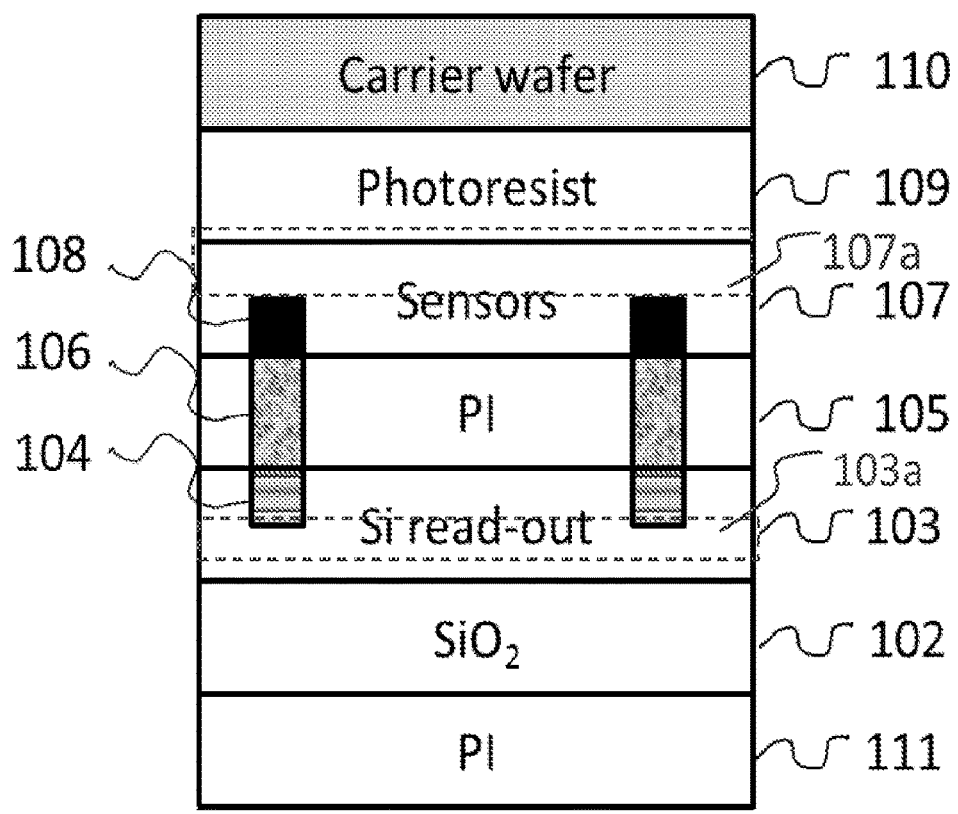
FIG. 1E is a schematic diagram of a stress neutral layer creation process of the first preferred embodiment integrated device fabrication method.
Figure 1F:
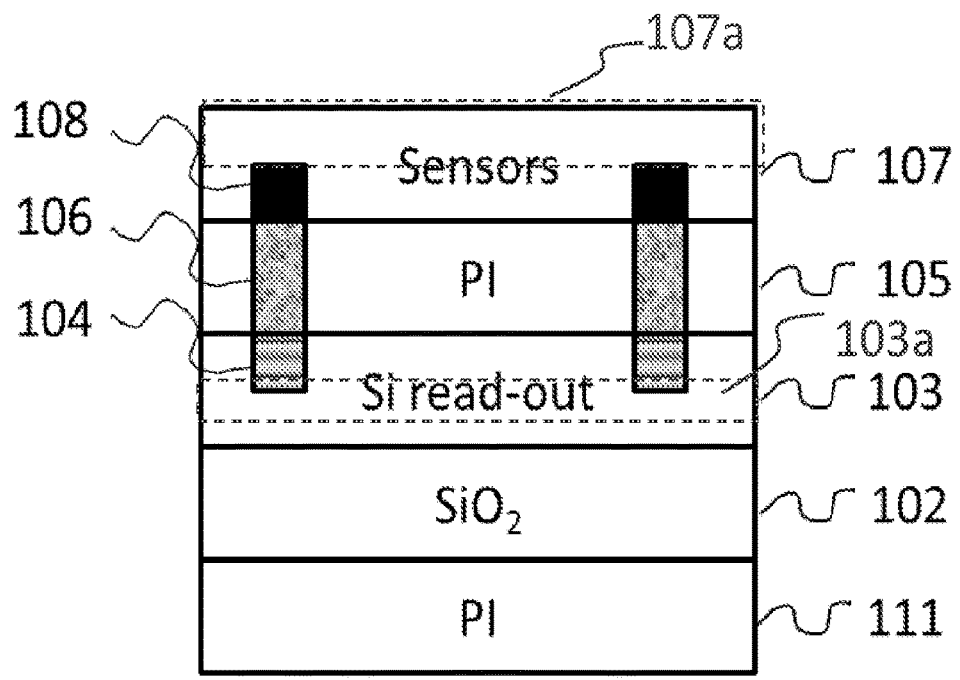
FIG. 1F is a schematic diagram of a preferred embodiment integrated thin film and high performance circuitry flexible device first preferred embodiment integrated device fabrication method.

FIGS. 1A-1F illustrate a preferred method for a CMOS compatible fabrication to produce an integrated device that includes a thin film element, which can be a biosensor to provide a device that is a wearable sensor. A preferred fabrication process provides wearable sensors. The fabrication process can be divided into two stages. FIGS. 1A-1C illustrate the fabrication of read-out, amplification, and transmission circuits, flexible polyimide sheets and sensors, all on an advanced substrate, silicon-on-insulator, and this substrate is built on a thick handle Si wafer underneath the insulator. FIGS. 1D-1F illustrate removal of the handle substrate, encapsulation of the flexible films, and use of the remaining functional flexible films for wearable electronics.

With reference to FIG. 1A, a first stage in the fabrication process begins with SOI (silicon-on-insulator) wafer including a bulk Si layer 101 an oxide layer 102 and top epitaxial silicon read out circuit layer 103. A high performance circuit 103a, such as a read-out circuit, is fabricated in the top epitaxial silicon circuit layer 103 using standard CMOS processing techniques, e.g. oxidation, photolithography, diffusion, electron-beam deposition, etc. Any suitable conventional fabrication technique for integrated circuits can be used to form the circuitry 103a, which can include conventional CMOS read out circuitry such as power management circuits, amplifiers, digitizers, filters, digital to analog convertors, and transceivers. Lithography masks and microelectronic circuit fabrication techniques can be used to form simple or complex read-out circuitry, which will be unaffected by subsequent steps of the preferred methods. The thickness of the top epitaxial layer preferably does not exceed 200 nm, to allow the fabrication of fully depleted CMOS devices; However, too thin of a layer may increase the series resistance and reduce the collected power from the microwire solar cells. At this stage, a pattern of metal connector pads 104 is also included in the mask for the read out circuit layer 103 for the purpose of forming interconnects between SOI CMOS read-out circuit and sensor layer that is formed on top of the read out circuit layer 103.

Next, a layer of dielectric 105 such as polyimide (PI) or parylene C is spin-coated or chemical-vapor deposited, respectively, on top of the fabricated read-out circuit layer 103 for passivation and to electrically isolate the read-out electronics from the sensors. The dielectric layer 105 serves as passivation layer for sensor electronics. Preferably, the dielectric layer 105 has a thickness of 2 μm to 10 μm. Preferably, the dielectric layer is polyimide. Polyimide has a mature process and is the most commonly used passivation film in industry. The thickness can be tuned from very thin (a few hundred nanometers) to very thick (a few tens of micrometers) and some polyimide types can be readily patterned by photolithography. The dielectric layer 105 is patterned by photolithography to expose contact vias 106 that accommodate electrical interconnects 106a down to the metal connector pads 104. Contact vias 106 can be filled with interconnect metal 106a using conventional deposition methods such as electron beam evaporation, sputtering, etc.

A sensor layer 107 with thin film elements, such as sensors 107a, is formed on top of the dielectric layer. The sensors 107a electrically connect to the interconnect metal 106 via contacts 108. The thickness of the sensor layer 107 is preferably less than 200 nm. The dielectric layer 105 must be preserved during formation of the sensor layer 107 and sensors 107a so that electrical isolation between the sensors 107a and the read out circuit 103a is maintained. In the example of using PI for the dielectric layer 105, this places an upper processing temperature limit for formation of the sensor layer 107 and sensors 107 at about 300° C. This limit is well above a thermal budget required for fabrication of the sensor layer 107 and sensors 107a. Standard photolithography, along with various deposition techniques such as sputtering, plasma-enhanced chemical vapor deposition (PECVD), atomic layer deposition (ALD), electron beam evaporation, spin-coating, spray-deposition, etc can be used to fabricate the sensors 107a. All of these processes have a thermal budget below 300° C. The sensors 107a are connected to the underlying read-out circuitry 103a by the vertical interconnection provided by the connector pads 104, the metal interconnect 106 and the sensor contact 108 through the dielectric layer 105.

A next phase of the fabrication process is processing to make the substrate flexible, and this phase is illustrated in FIGS. 1C-1F. Major steps in this phase include bonding to a temporary carrier wafer, etching the bulk silicon, and then removing the carrier wafer.

FIG. 1C illustrates the result of spin-coating a layer of polymer 109, e.g., photoresist onto the sensor layer 107. A carrier wafer 110 is then placed on top of the polymer 109. Heating is used to bond the carrier wafer to the polymer. Heating with a hot plate, for example, will harden the polymer and create a bond between the carrier wafer 110 wafer and polymer 109.

Next, the bulk Si wafer 101 is removed. This can be done by flipping the completed chips and removing the Si layer from the SOI stack by deep reactive ion etch (RIE) or by wet chemical etching. In particularly preferred embodiments, dry etching is used and no wet etching is required. The silicon etching process stops at the buried silicon dioxide layer 102, as seen in FIG. 1D, leaving the oxide layer 102 exposed. The Si wafer 101, prior to removal, constitutes the thickest portion of the device (300 μm or more) the device structure. Once removed, the remaining layers, excluding the carrier wafer 110, which will also be removed, are flexible. A total thickness <~50 μm is preferred, and the thickest remaining layer is the dielectric layer 105. Total thickness is more preferably equal to or less than ~20 μm, and embodiments that are ~10.5 to 11 μm or less in total thickness are most preferred and are very thin and flexible. The thin, flexible substrate and small size (pin head sized) of preferred embodiments allows the resulting device shown in FIG. 1F to be easily integrated into wearable everyday items, like watches, jewelry, clothes, etc.

FIG. 1E shows that another second layer of polymer 111, e.g., photoresist is spin coated onto the exposed oxide layer 102. The polymer 111 is preferably photoresist that has the same thickness as the dielectric 105, which helps to keep the CMOS read-out circuit 103a in a neutral stress plane. The maximum thickness of this layer is 10 μm in preferred embodiments.

FIG. 1F illustrates the final step in the fabrication of the device, which is to remove the temporary carrier wafer 110 by dissolving the polymer. In the case of photoresist, this can be accomplished in an acetone bath. An acetone bath does not affect the other layers of the integrated device shown in FIG. 1F. The FIGS. 1A-1F fabrication showed one device, but the methods permit the monolithic fabrication of thousands of devices on a single wafer. The final devices can be separated via dicing, which can be accomplished by photolithography and etching.

The resulting integrated sensing and read-out device includes preferred materials shown in FIGS. 1A-1F. The finished device in FIG. 1F consists of the silicon dioxide layer 102, the read-out CMOS circuitry layer 103 sandwiched between two layers of polyimide 105, 110, and the exposed sensors 107a. Example sensors include biological sensors, for example EEG and EMG sensors. Other sensors include temperature, pressure, radiation and ionic/chemical sensors. Experiments have demonstrated the feasibility of the FIGS. 1A-1F fabrication method for a simple device structure by successfully creating a flexible circuit starting from an SOI wafer.

Figure 1G:
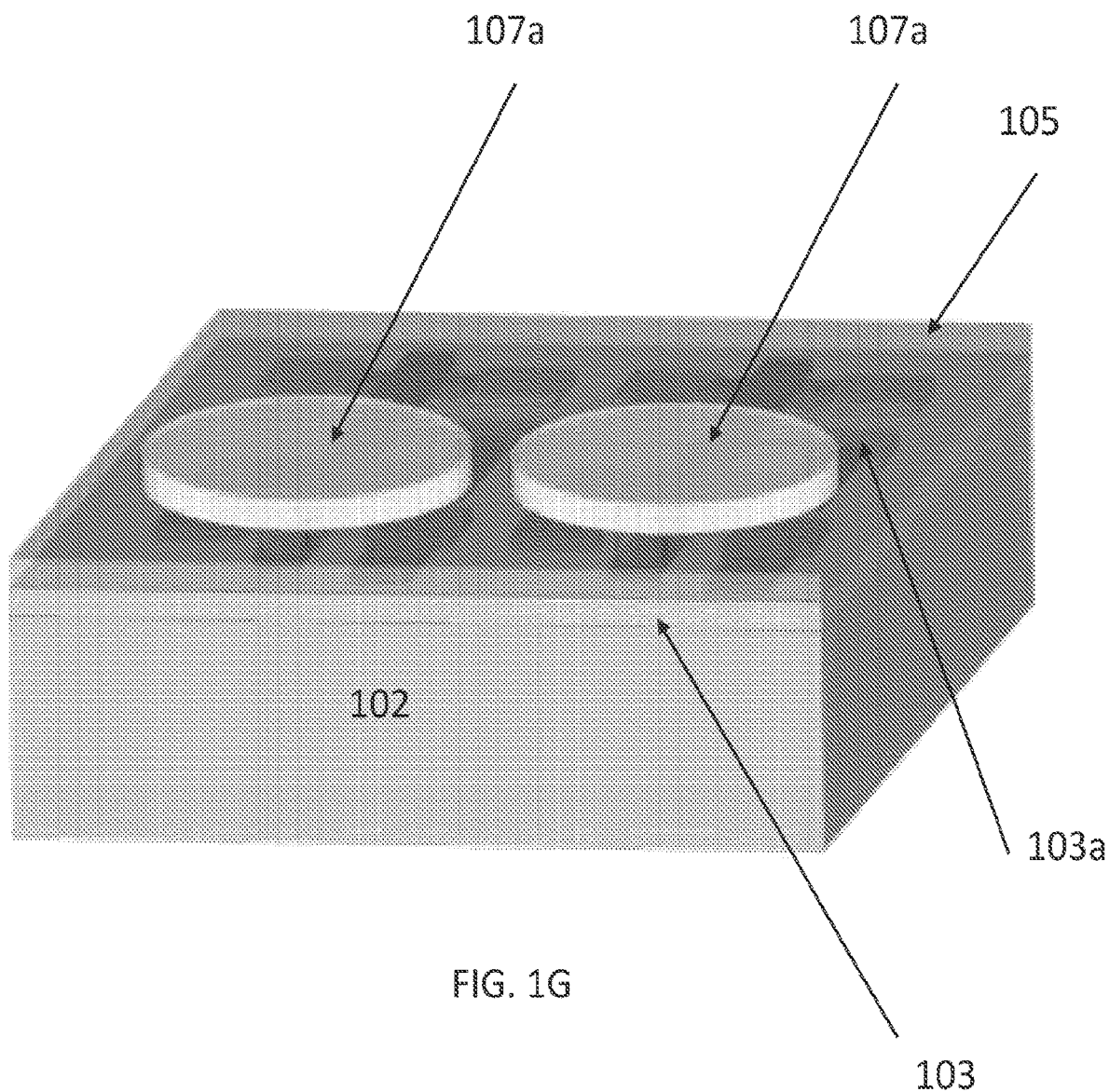
FIG. 1G is a perspective view that illustrates the formation of thin film elements in FIG. 1B.

EEG and EMG sensors have been fabricated on arbitrary substrates. FIG. 1G illustrates the sensor electrodes 107a in FIG. 1B. The electrodes have a substantial area that can encompass a substantial, e.g. more than 20-30% of the surface of the device and are exposed for epidermal contact. In example experimental embodiments, the electrodes each had a surface area of a few hundred $\mu m^2$, e.g. 400 $\mu m^2$. The electrodes 107a are formed over the vias 106, and can occupy a substantial area of the top of the layer 107.

Figure 1H:
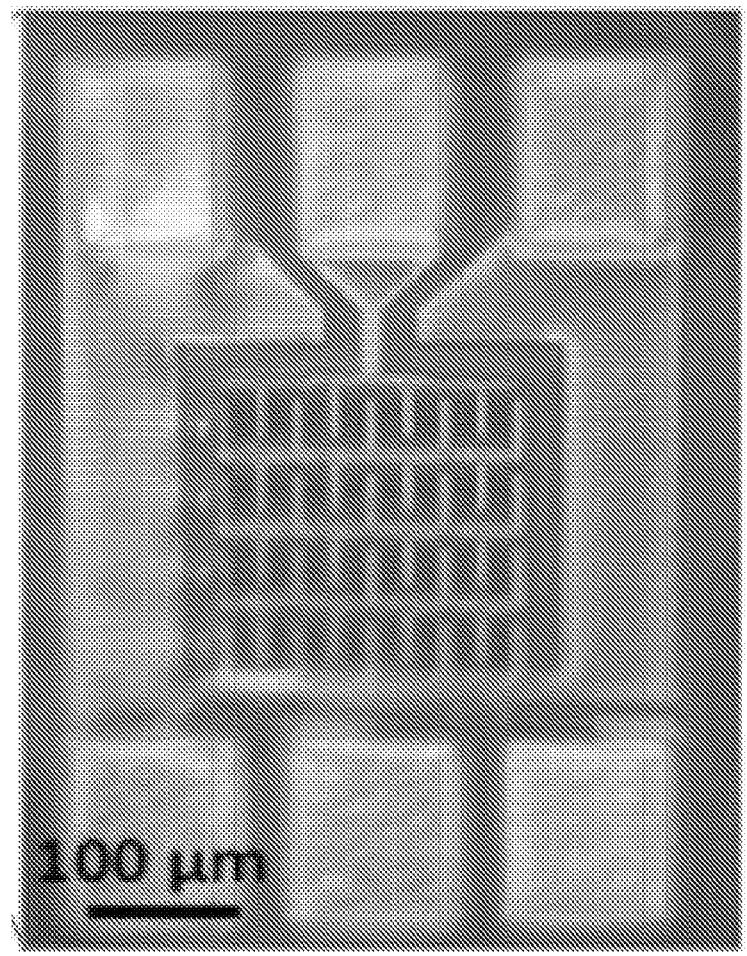
FIGS. 1H-1I are images of an example integrated device from a standard 0.18 μm complementary metal oxide (CMOS) MOISIS foundry service that was monolithically integrated with thin flexible substrates in a method consistent with FIGS. 1A-1F and for a total device thickness of ~9.5 μm.
Figure 1I:
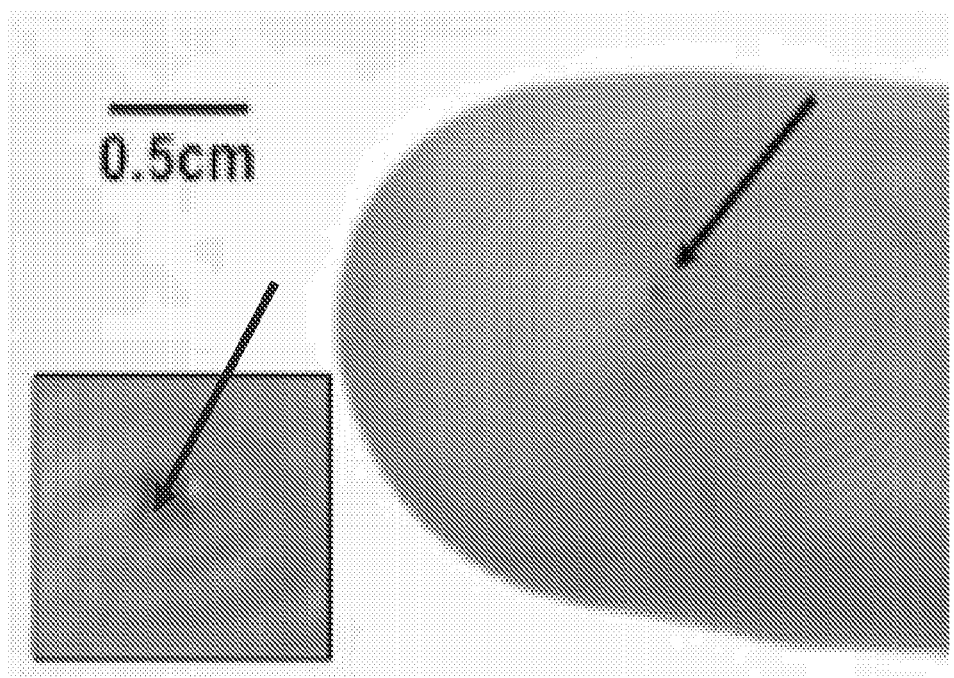

The monolithic integration process of FIGS. 1A-1F provides high performance electronics monolithically integrated with sensors or other thin film elements, and the electronics 103a are fabricated during the process. The read-out electronics 103a can also be fabricated in advance and then the process continued as in FIG. 1A to monolithically integrate the sensors with the electronics. This was demonstrated experimentally, and the fabricated device is shown in FIGS. 1H and 1I. The methods of the invention demonstrated the ability to create an integrated device that is 1000× smaller than state of the art (Kim et al., Science 2011) devices. An entire integrated device can be less than 0.5 cm by 0.5 cm in footprint. An example integrated device formed according to present methods included 0.18 μm CMOS devices trough a MOISIS foundry process embedded in a 9.5 μm thick flexible integration. This device is shown in FIGS. 1H and and 1I with example scaling.

Figure 2A:
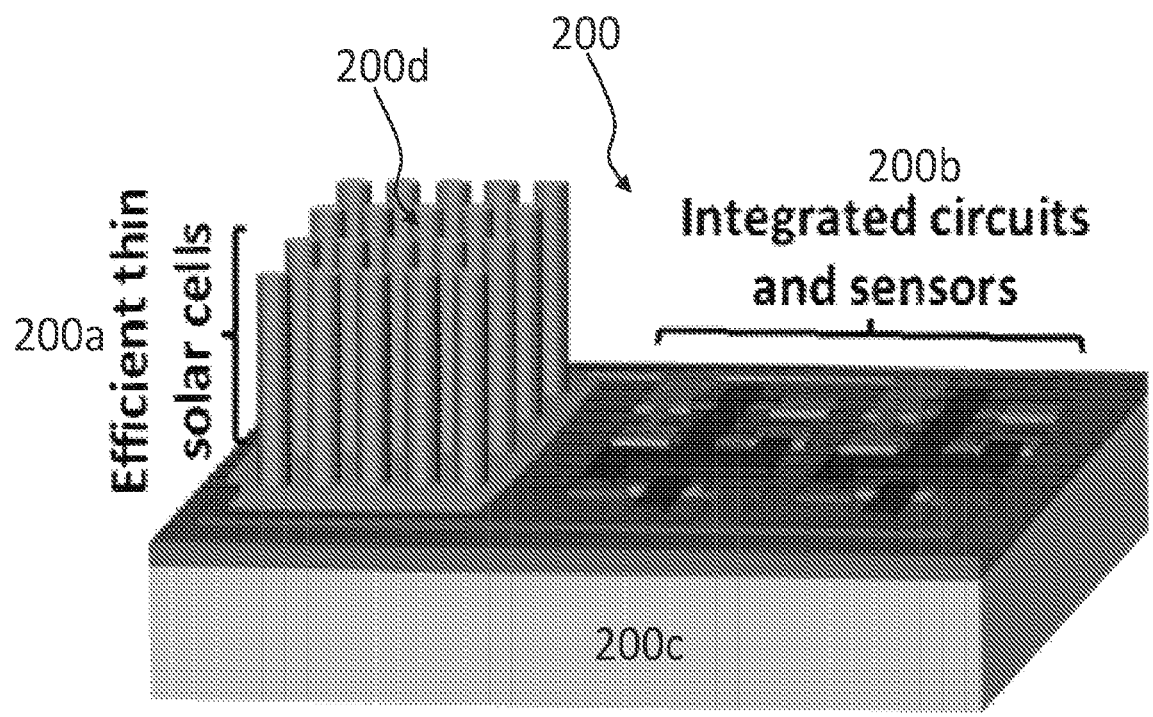
FIG. 2A is a perspective view illustrating a second embodiment integrated power source, thin film device and integrated circuitry flexible device.

Preferred embodiments also provide solar powered self-contained high performance integrated thin film elements/devices and circuits, as represented by an integrated device 200 shown in FIG. 2A. The device includes a solar cells 200a integrated with thin film sensors and circuits 200b on a substrate 200c. The thin film devices are not shown, but would be on the bottom of the device opposite the circuits 200b. The circuits 200b are represented simply as a single FET device, but can include and entire complex circuit of arbitrary behavior. Any number of FETs can be fabricated and connected via standard CMOS processing as needed using a preferred fabrication method of the invention, as illustrated in FIGS. 2B-2F for forming a solar cell and in FIGS. 3A-3D for integrating sensors and circuits adjacent the solar cell 200a.

The preferred device 200 consists of at least 2 parts: a power source, in the form of solar cell 200a in FIG. 2A, and an electronic circuit and sensor circuit section 200b. The sensors are on the opposite side of the FIG. 2A structure (as in FIGS. 1A-1F) and are connected through vias through the oxide layer 200c (which corresponds to the oxide layer 105 in FIG. 1F). Additional preferred embodiments include more parts, such as a charge storage element (e.g., a capacitor), and any type of sensors or transducers, including those made from compound semiconductor materials. Such components can be fabricated on the same oxide layer 200c of the power source and the electronics, and will not be adversely affected by subsequent processing. The solar cell 200a includes a plurality of microwire silicon sensing elements 200d. In preferred embodiments, state of the art integrated circuit technology (e.g., 14 nm node electronics) can be fabricated by the FIGS. 1-F method or by the method of FIGS. 2B-2F. This provides high performance devices and allows the circuits to occupy a very small area. The overall device can then be very small while still permitting sufficient area for the solar cells. In example embodiments, the monolithically integrated sensing/read-out/solar device has a length and width of about 0.5 mm to 5 mm. Approximately 80% of the area is dedicated to the solar cell, and the remaining 20% is used by capacitors and read out electronics.

Figure 2B:
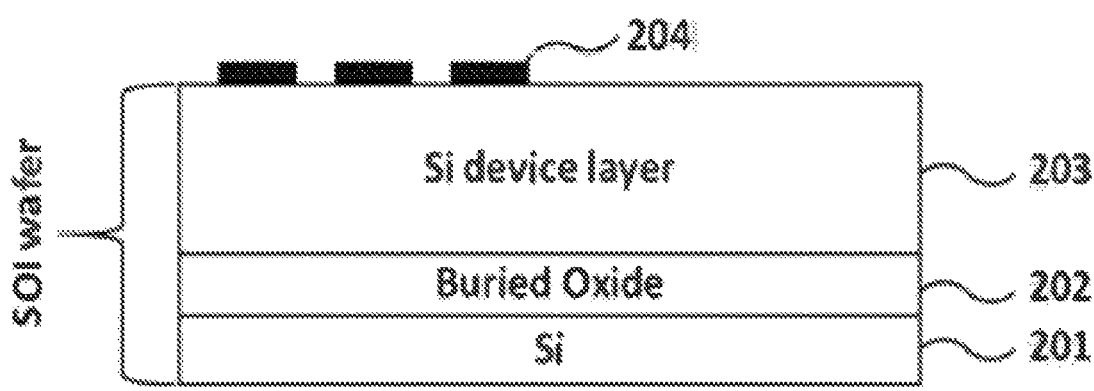
FIG. 2B is a schematic view of a mask formation process of a second preferred embodiment integrated device fabrication method.
Figure 2C:
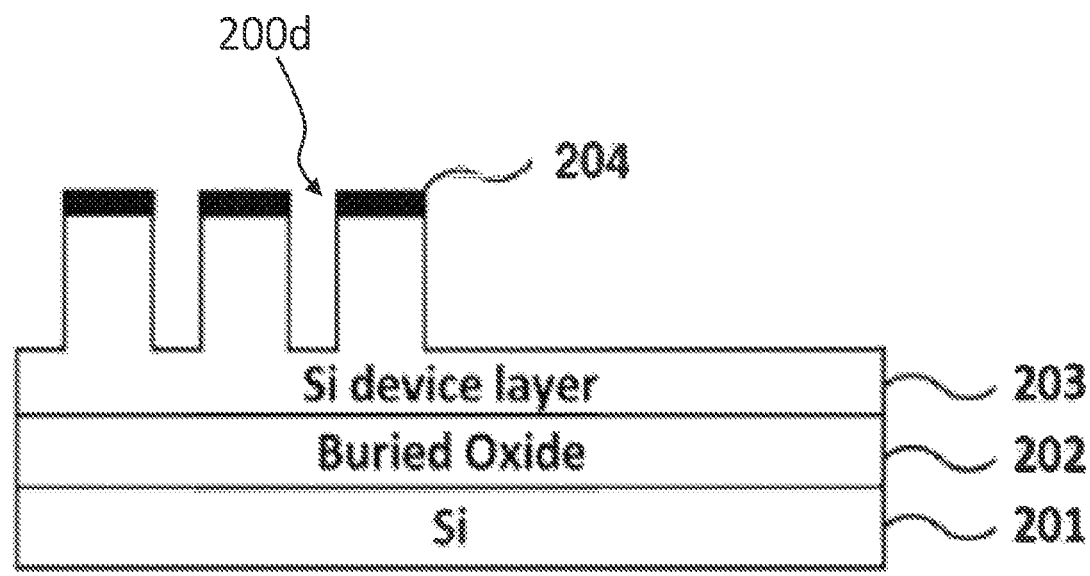
FIG. 2C is a schematic view of a micro wire etching process of a second preferred embodiment integrated device fabrication method.
Figure 2D:
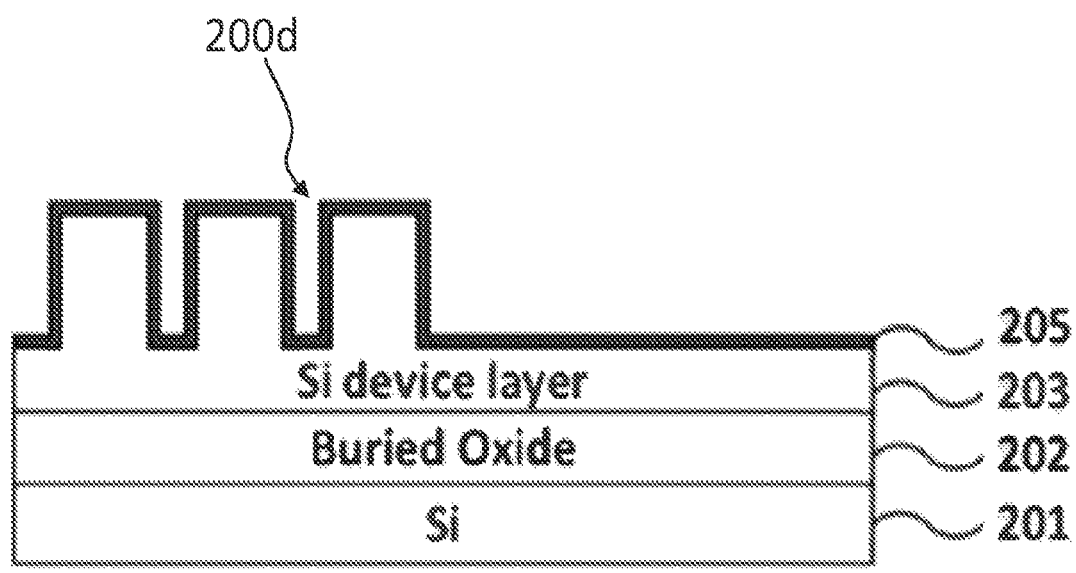
FIG. 2D is a schematic view of an oxide layer process of a second preferred embodiment integrated device fabrication method.

FIG. 2B shows that the fabrication starts with a clean silicon-on-insulator including bulk silicon 201, an oxide 202 and a device layer 203. The device layer 203 Si is doped p-type. The device layer can also be n-type, but p-type is preferred because p-type provides a better substrate for long photogenerated minority electron diffusion length, i.e., more efficient solar cell, and NMOS transistors with higher electron mobility. The method could also begin with bulk silicon, and then form the oxide layer 202 and device layer 203. A microwire solar cell mask is used to create regions to define the patterns and the locations of microwires that form the solar cell 200a. An etch mask 204 is formed on the silicon device layer. The etch mask 204 is a preferably a patterned layer of metal, such as Ni. The mask 204 can be deposited, for example, by electron-beam evaporation. FIG. 2C illustrates the result of etching that forms the microwire sensing elements 200d. In a preferred embodiment, an inductively coupled plasma reactive ion etch (ICP-RIE) is performed until the desired microwire height is achieved. In a preferred embodiment, the microwire height is (~8.5-10 µm). The 10 µm height is preferred. After about 10 µm the microwires tend to have ill-formed ends. The diameter of wires is 2-3 µm to match the minority carrier diffusion length. After removing the etch mask 204 and cleaning the surface of the wafer to remove any residues, the entire device is thermally oxidized, e.g., at 1100° C., to form a thin SiO$_2$ layer 205, which is then removed by BOE (buffered oxide etch) in order to smoothen the side-walls of the microwires 200d. The relatively high 1000° C. temperature is preferred so that the oxidation happens more quickly. This smoothing process reduces recombination on the surface of microwire solar cells and it can be repeated multiple times until the desired smoothness is achieved. However, experiments have shown that single oxidation typically produces nanometer level smoothness and is therefore sufficient. A layer of SiNx 206 is deposited by plasma-enhanced chemical vapor deposition (PECVD), and then selectively patterned using photolithography and wet-etch. The pattern removes the SiNx 206 from all areas except the areas where the Si must be protected from the diffusion of p-type (if substrate is n-type) or n-type (if substrate if p-type) dopant. A p-type or an n-type diffusion is performed using a source wafer 207 that is covered with spin-on-dopants (phosphorous if substrate is p-type and boron if substrate is n-type) 208, in close proximity to the sample at doping temperature, e.g., high temperature (e.g., 1000° C.), using rapid thermal annealing or another method of doping. The doping concentration of the created doped area 209 shown in FIG. 2F is usually in the range of $10^{18}$ cm$^{-3}$-$10^{19}$ cm$^{-3}$ and is higher than the original substrate doping concentration which is found to be optimal at about $5\times10^{16}$ cm$^{-3}$. The junction depth is preferred to be of the order of 60 nm-100 nm, not too thin to resolve series resistance problems in the n+ outermost layer to the solar cell surrounding contacts, and not too deep to prevent excessive Auger recombination in this layer. This completes the formation of the solar cell 200a. The proximity doping process with a spun-on layer of dopant used as the source is very effective at producing a high-quality shell junction, which provides the basis for carrier separation in the p-n microwire solar cell elements. The proximity doping is therefore preferred. The inventors also believe that a modified gas phase doping process can be used. The creation of a deep junction is to be avoided, and the modified gas doping process deposits a thin layer of dopant on the surface and then short-time anneals to create activate the dopants in the shallow junction. Methods of the invention create solar cells with shallow radial p-n junctions that are monolithically integrated with CMOS transistors.

Figure 2E:
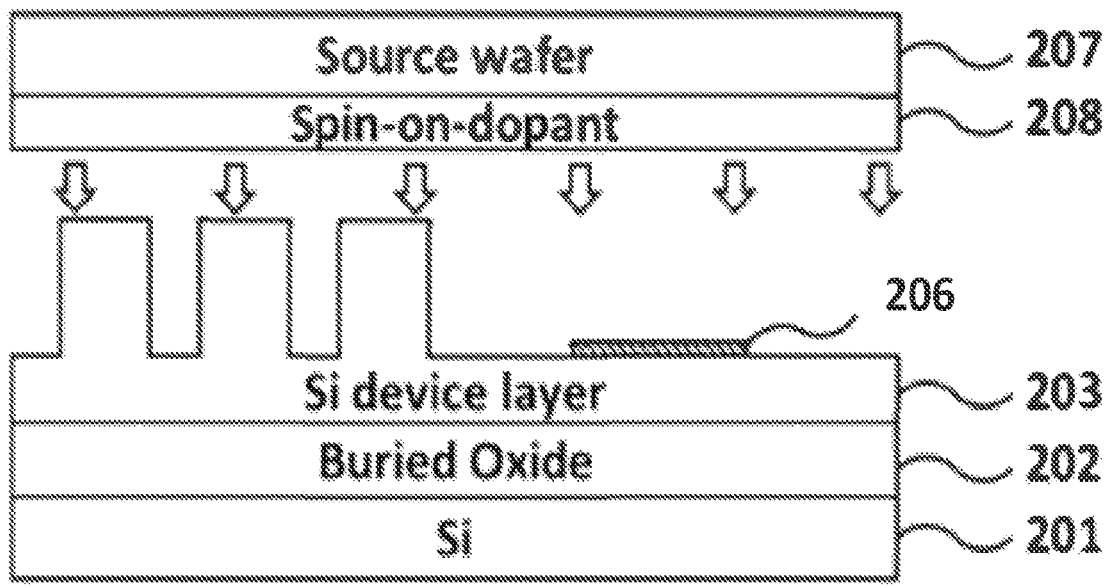
FIG. 2E is a schematic view of a selective proximity doping process of a second preferred embodiment integrated device fabrication method.
Figure 2F:
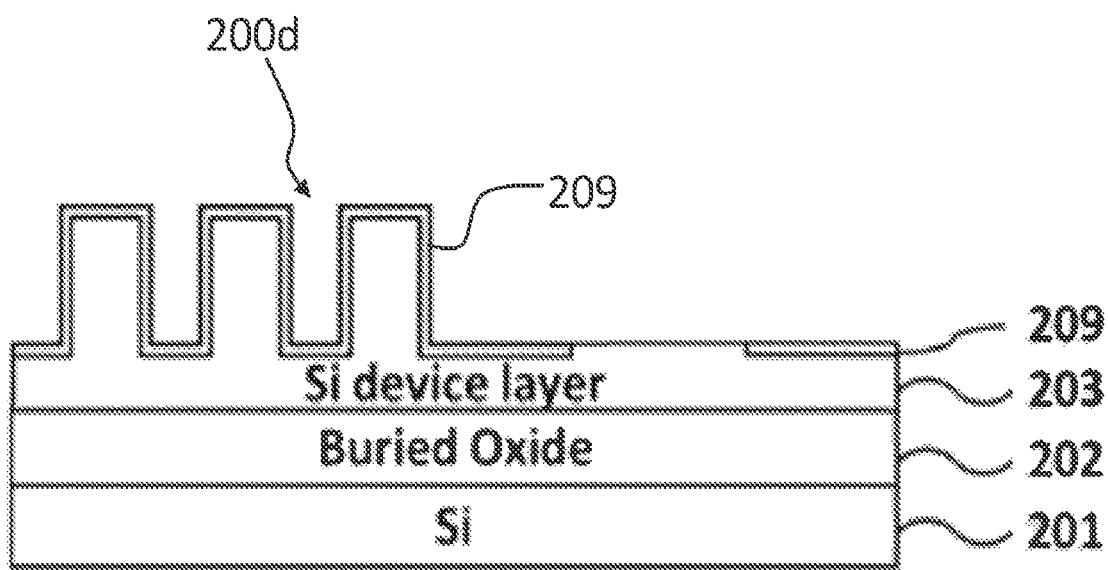
FIG. 2F is a schematic view of a completed solar cell device of a second preferred embodiment integrated device fabrication method.
Figure 3A:
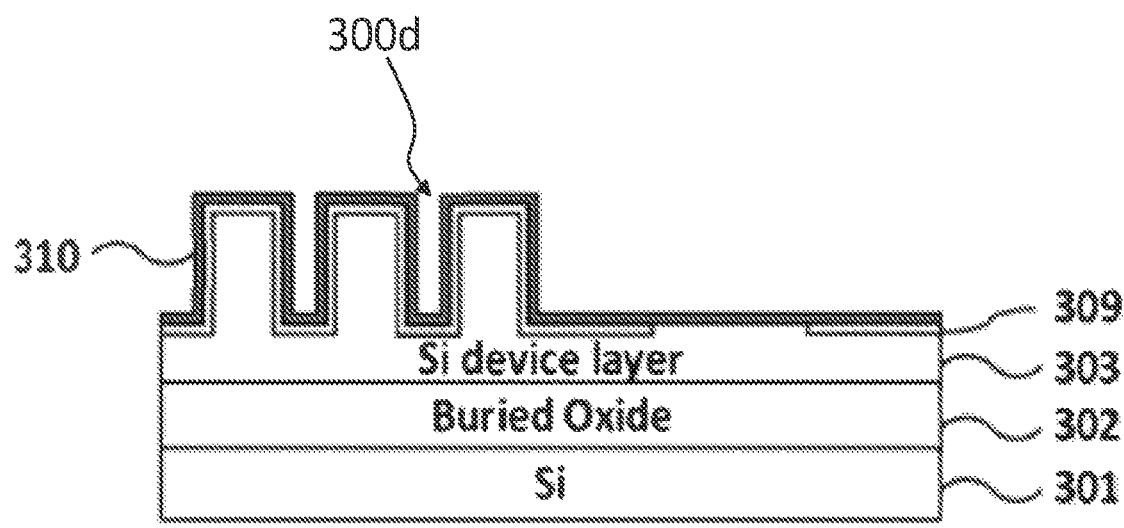
FIG. 3A is a schematic view of a thin (~10 nm) passivation oxide formation process applied to the FIG. 2F solar cell device and that will simultaneously act as a gate-oxide layer for adjacent CMOS devices.
Figure 3B:
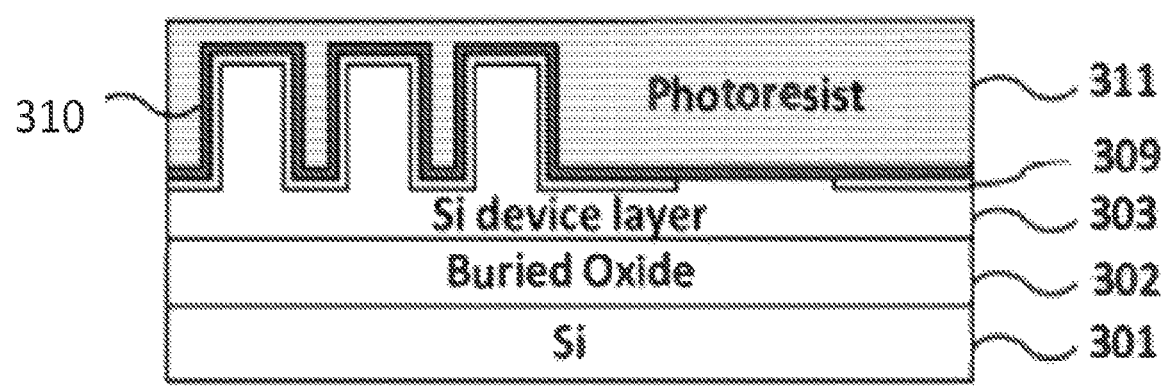
FIGS. 3B-3C are schematic views of a photoresist patterning process applied to the FIG. 3A device.
Figure 3C:
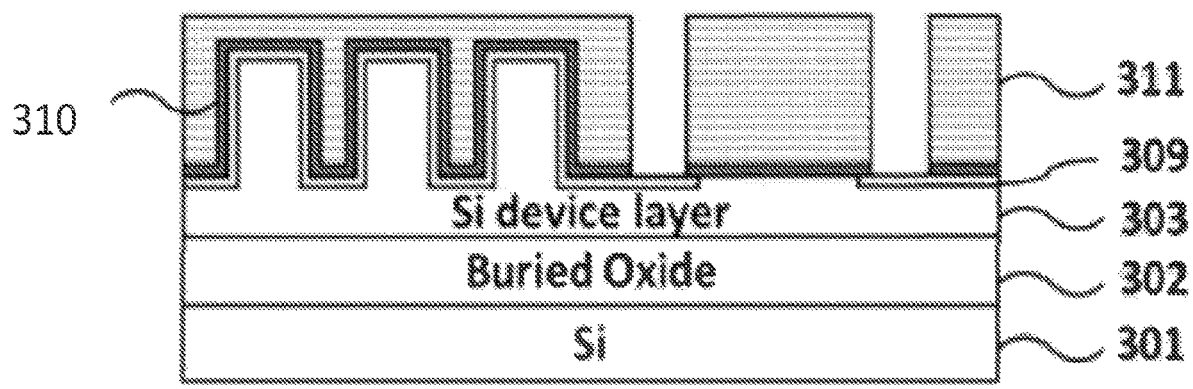

FIGS. 3A-3D illustrate a preferred method for fabricating sensors and circuits on the completed solar cell of FIG. 2F. The latter two digits of reference numbers in FIGS. 3A-3D are the same as corresponding parts in FIGS. 1A-2F. After completion of the doping to create the doped regions 309, the masking SiNx layer 206 is removed and a thin SiO$_2$ layer 310 is formed by thermal oxidation to serve two purposes: a passivation layer for the solar cell and as a gate dielectric for the adjacent transistors, as shown in FIG. 3A. Alternatively, a different material may be substituted as the gate dielectric layer 310 to improve device performance, for example, Al$_2$O$_3$, HfO$_2$, etc, using any deposition method (PECVD, atomic layer deposition, e-beam evaporation, sputtering, etc.). This layer 310 also covers the solar cell microwires 300d to passivate surfaces of the microwires 300d. In FIG. 3C, a masking step with patterned photoresist 311 is performed via photolithography to define vias to make contact to the source and drain regions of FETs that will be formed. Etching of gate dielectric is performed to open vias to the source/drain regions of FETs and prepare for the electrode metallization using any etching method, for example, RIE. Device contacts and interconnects 312 are deposited to create the contacts for source/gate/drain regions and to connect the solar cells in a desired pattern, such as in series, as well as to connect the microwire solar cells with the electronics. Multiple solar cells can be connected in series to obtain the desired output voltage if necessary. The integrated circuit processes permitted by the fabrication methods of the invention can form a wide variety of circuit components. FETs and thin film sensors have been mentioned. Additional integrated circuit features include thin-film battery electrodes that can be deposited layer-by-layer and patterned to store energy harvested by the solar cell. The complete system can thus have energy harvesters (solar cells), energy storage elements (thin film batteries or super-capacitors), electronic circuits for power regulation and signal conditioning, and electrophysiological and chemical sensors. The layer by layer fabrication methods that provide the integration of the solar cell on the substrate permit a wide variety of devices to then be co-fabricated on the same monolithic structure, leveraging the same device layer.

Figure 3D:
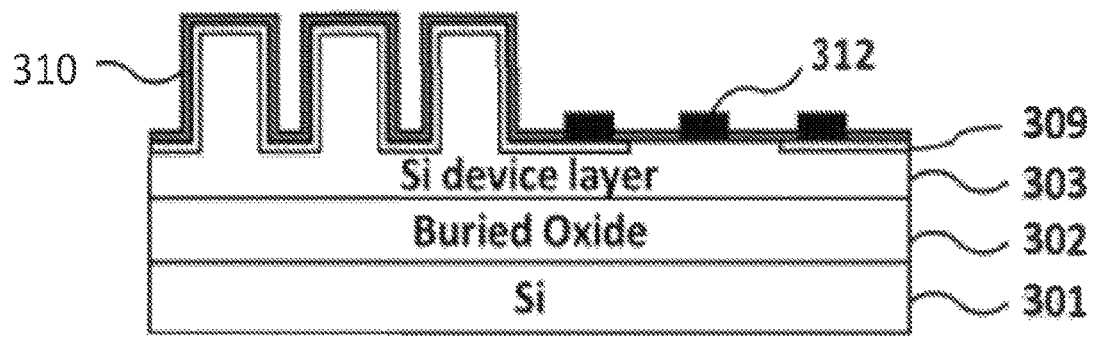
FIG. 3D is a schematic view of metal contact and interconnect formation process of applied to the FIG. 3C device.
Figure 3E:
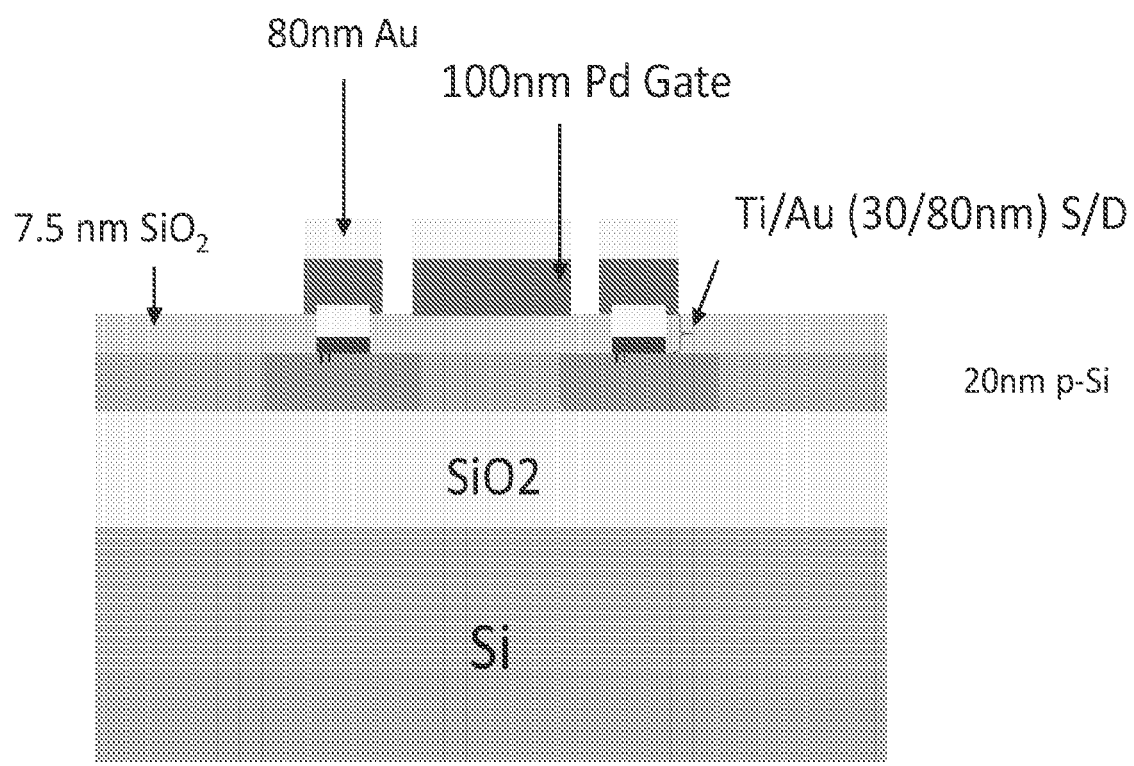
FIG. 3E is a schematic view of a proximity doped FET that was formed in an experiment to demonstrate the device fabrication on an SOI wafer consistent with proximity doping of FIG. 2E and the device fabrication of FIGS. 3A-3D.

FIG. 3E illustrates an example device formed experimentally via the proximity doping process of FIG. 2E and the fabrication steps of FIGS. 3A-3D. The source and drain contacts were a layer stack of Ti/Au/Pd/Au. The Ti was 30 nm, the first Au 80 nm, the Pd 100 nm and the top Au 80 nm. The gate contact was a stack of Pd/Au. The gate oxide was 7.5 nm thick $SiO_2$. The device layer was 20 nm p-Si. The FIG. 3E device is an example FET that can be fabricated in accordance with preferred methods. The threshold voltage of example nMOS devices was from 0.5 to 0.65 V. The threshold voltage of example pMOS devices was −0.2 to −0.5 V. The experimental fabrication showed the ability to produce low threshold devices and integrate the device into circuits in a single fabrication process onto a common substrate with solar cells.

Preferred experimental embodiments have been demonstrated experimentally with 10 µm-tall junction Si microwire solar cells with 1×1 $mm^2$ area that operate with open circuit voltage of 0.54 V, short circuit current of ~35.11 $mA/cm^2$, and fill-factor of 0.79 resulting in ~15% power conversion efficiency. The microwire sensing elements of the solar cells were formed according to FIGS. 2B-2F. Operational MOSFET devices were fabricated according to FIGS. 3A-3D, which demonstrated the ability to integrate solar cell and MOSFET devices in a single wafer.

Figure 4A:
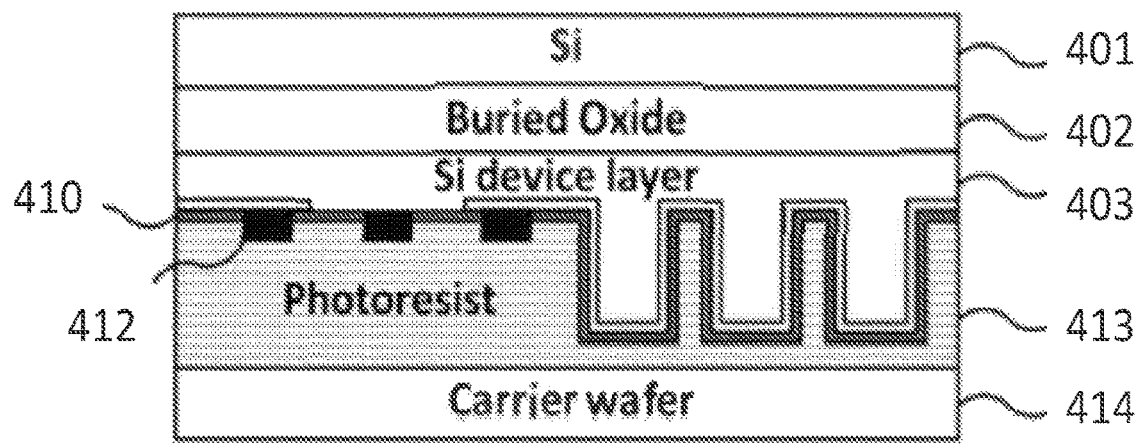
FIG. 4A is a schematic view of a layer removal process of applied to the FIG. 3D integrated device.
Figure 4B:
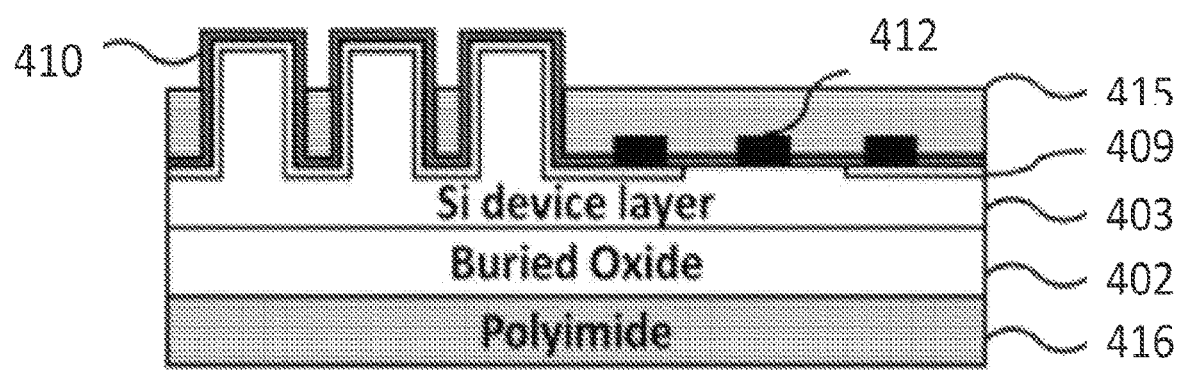
FIG. 4B is a schematic view of a stress neutral layer creation process applied to the FIG. 4A integrated device.

FIGS. 4A and 4B illustrate steps to create a flexible device from the completed integrated solar cell device of FIG. 3D. The latter two digits of reference numbers in FIGS. 4A-4B are the same as corresponding parts in FIGS. 3A-3D. The process for making the FIG. 3D flexible follows the use of a carrier wafer and removal of the bulk Si as in FIGS. 1C-1F and FIGS. 3B-3D. Thus, after attachment of a carrier wafer 414 via polymer in FIG. 4A, the device can be made flexible by etching the Si layer 401 from the bottom of the substrate using an ICP-RIE or wet etch process. The dry etching is most preferred. Preferably, the top layer of the completed device is covered with photoresist 413 for protection then flipped and temporally transferred on the carrier wafer 414, followed by an ICP-RIE of the Si handle layer 401. When an SOI wafer was used as a substrate for solar cell and integrated sensor and circuit fabrication, etching is stopped when the buried oxide layer 402 is reached. After separating the device from the carrier wafer 414 and removing photoresist 413, the top and the bottom of the flexible device are covered by a polymer layers top 415 and bottom 416. As discussed above, the polymer layers are preferably the same thickness to keep the integrated circuit layers in a neutral stress plane. The deposition process for the layers 415 and 416 can include drop-casting, spin-coating, etc.

Figure 5A:
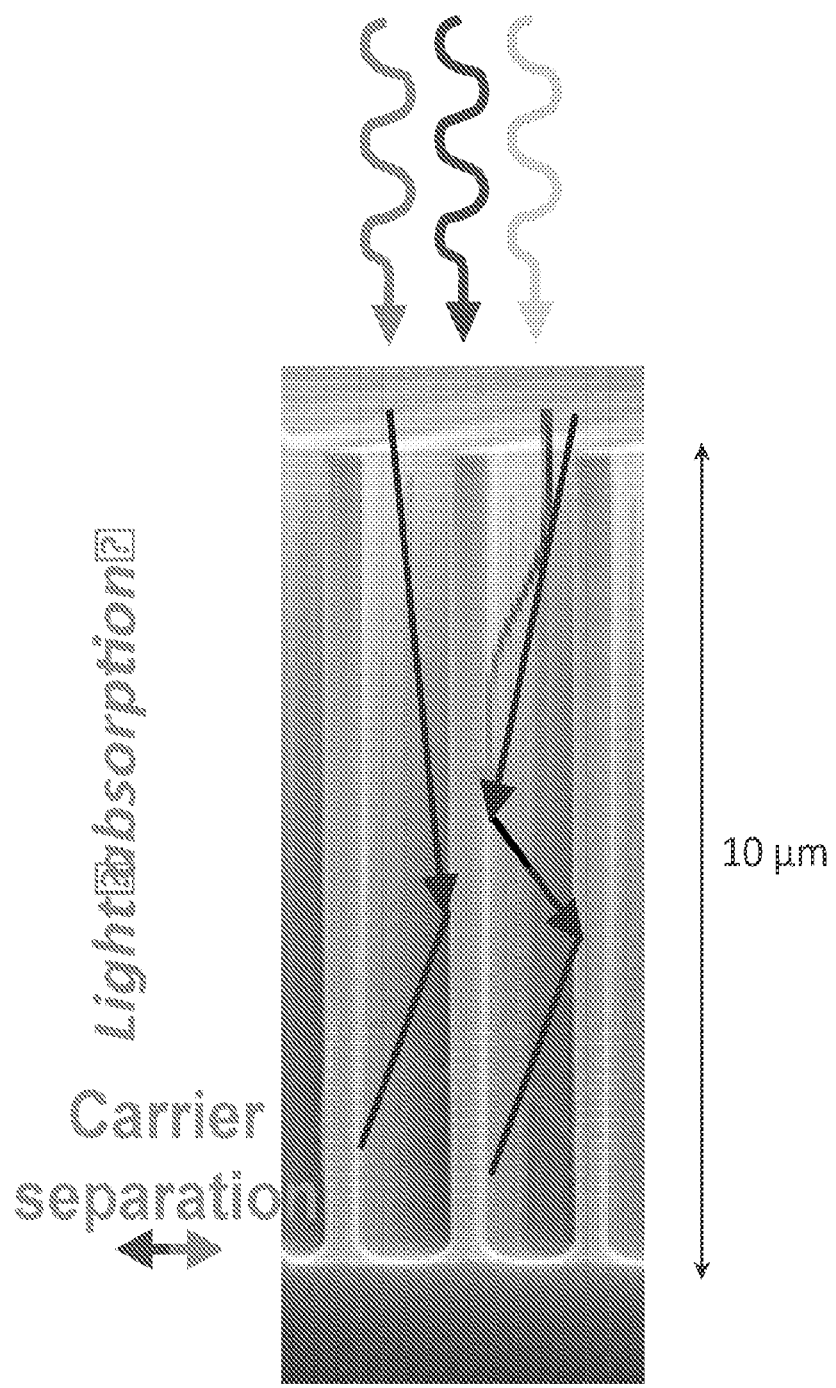
FIG. 5A is labeled image of a portion of the solar cell of an experimental integrated device formed in accordance with FIG. 2A.
Figure 5B:
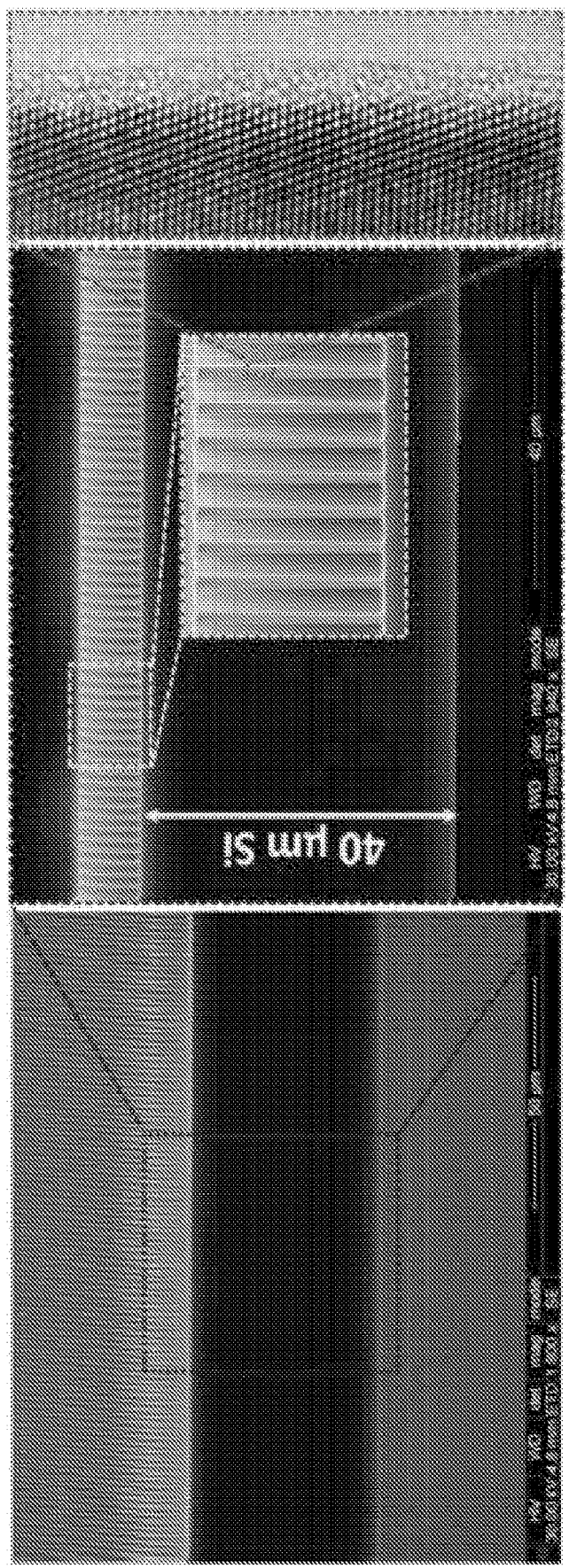
FIG. 5B includes images of an array of nanowires closely spaced as in an solar cell in preferred embodiments.

FIG. 5A is labelled image of a portion of an experimental solar cell that was fabricated as an integrated device consistent with FIG. 2A, according to the methods in FIGS. 2B-4B. The microwires were about 10 µm in length and had a base of 2-3 µm. The diameter is preferred to match the minority carrier diffusion length. Microwires are preferably as long as possible, but become less uniform above about 10 µm in length. Light waves are absorbed along the length of the microwires, and carrier separation is achieved radially across the microwires. Individual elements can be closely packed, the microwires can be spaced, for example at 0.5 to 2 µm separations. FIG. 5B shows images of a large array of microwires formed closely packed.

While specific embodiments of the present invention have been shown and described above and in the attachments following the example claims, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A monolithically integrated device, comprising,
a polymer base layer;
an oxide layer adhered to the polymer base layer;
a CMOS circuitry epitaxial layer that does not exceed 200 nm in thickness on top of the oxide layer;
a polymer dielectric layer on top of the CMOS circuitry epitaxial layer, the polymer dielectric layer having a thickness in the range of 2 µm to 10 µm;
a thin film device layer formed on the polymer dielectric layer, the thin film device layer having thickness of less than 200 nm;
contact vias through the polymer dielectric layer;
interconnect metal in the contact vias connecting the CMOS circuitry to the thin film device layer, wherein a total thickness of the monolithically integrated device is less than ~50 µm thick.

2. The device of claim 1, comprising a sensor device, wherein the thin film device layer comprises a sensor and the CMOS circuitry epitaxial layer comprises a read-out circuit.

3. The sensor device of claim 2, wherein the sensor device is less than ~20 µm thick.

4. The sensor device of claim 3, wherein the total thickness is in the range of ~10.5 to 11 µm.

5. The device of claim 1, wherein the polymer dielectric layer has a thickness of 2 µm to 10 µm.

6. The device of claim 1, wherein the polymer dielectric layer comprises polyimide or parylene C.

7. The device of claim 1, wherein the polymer dielectric layer consists of polyimide.

8. The sensor device of claim 2, comprising a plurality of sensors, wherein the sensors are exposed for epidermal contact.

9. The device of claim 1, wherein the thin film device layer comprises a biosensor.

10. The device of claim 1, wherein the thin film device layer comprises a thin film battery, a biosensor or an environmental sensor, and the CMOS circuitry epitaxial layer comprises a read-out circuit.

11. The device of claim 1, comprising:
a silicon dioxide layer, the CMOS circuitry epitaxial layer being upon the silicon dioxide layer; and
a bottom polymer layer adhered to the silicon dioxide layer.

12. The device of claim 1, wherein the polymer base layer and the polymer dielectric have the same thickness to keep the CMOS circuitry epitaxial layer in a neutral stress plane.

13. A monolithically integrated device, comprising:
a CMOS circuitry epitaxial layer including a CMOS circuit;
a polymer dielectric layer on top of the CMOS circuitry epitaxial layer covering the CMOS circuit, the polymer dielectric layer having a thickness in the range of 2 µm to 10 µm;
doped microwires extending from the CMOS circuitry epitaxial layer extending through the polymer dielectric layer defining a shallow solar cell junction therein, wherein the solar cell junction depth is 60 nm-100 nm; and connection between the solar cell junction and the CMOS circuitry to power the CMOS circuitry, wherein a total thickness of the monolithically integrated device is less than ~50 μm thick.

14. The device of claim 13, wherein the microwire array solar cell comprises a plurality of individual, spaced apart doped microwires and the shallow junction comprises a shell p-n junction.

15. The sensor device of claim 14, wherein the microwires are in the range of 8.5-10 μm long and about 2-3 μm in diameter.

16. The device of claim 13, wherein the shallow solar cell junction is doped to a concentration of $10^{18}$ cm$^{-3}$-$10^{19}$ cm$^{-3}$.

17. The sensor device of claim 16, wherein microwires are doped beyond the shallow junction to about $5\times10^{16}$ cm$^{-3}$.

* * * * *